United States Patent
Lee et al.

(10) Patent No.: US 9,902,969 B2
(45) Date of Patent: Feb. 27, 2018

(54) VECTOR COMPRISING GENE FRAGMENT FOR ENHANCEMENT OF RECOMBINANT PROTEIN EXPRESSION AND USE THEREOF

(71) Applicant: KOREA RESEARCH INSTITUTE OF BIOSCIENCE AND BIOTECHNOLOGY, Daejeon (KR)

(72) Inventors: Eun Gyo Lee, Daejeon (KR); Hong-Weon Lee, Daejeon (KR); Shin Young Kang, Daejeon (KR); Yeon-Gu Kim, Daejeon (KR); Joon Ki Jung, Daejeon (KR); Jungoh Ahn, Daejeon (KR); Seung Hee Kang, Daejeon (KR); Chun Sug Kim, Daejeon (KR); Hyeok Won Lee, Daejeon (KR); Jin Gyeom Lee, Daejeon (KR)

(73) Assignee: KOREA RESEARCH INSTITUTE OF BIOSCIENCE AND BIOTECHNOLOGY (KR)

( * ) Notice: Subject to any disclaimer, the term of this patent is extended or adjusted under 35 U.S.C. 154(b) by 0 days.

(21) Appl. No.: 15/319,273

(22) PCT Filed: Jun. 16, 2015

(86) PCT No.: PCT/KR2015/006098
§ 371 (c)(1),
(2) Date: Dec. 15, 2016

(87) PCT Pub. No.: WO2015/194834
PCT Pub. Date: Dec. 23, 2015

(65) Prior Publication Data
US 2017/0218392 A1   Aug. 3, 2017

(30) Foreign Application Priority Data

Jun. 17, 2014 (KR) ........................ 10-2014-0073443

(51) Int. Cl.
| | | |
|---|---|---|
| *C12N 15/85* | (2006.01) | |
| *C12Q 1/68* | (2018.01) | |
| *C07K 14/435* | (2006.01) | |
| *C07K 16/00* | (2006.01) | |

(52) U.S. Cl.
CPC ........ *C12N 15/85* (2013.01); *C07K 14/43595* (2013.01); *C07K 16/00* (2013.01); *C12Q 1/6876* (2013.01); *C12Q 1/6897* (2013.01); *C07K 2317/14* (2013.01); *C12N 2840/203* (2013.01); *C12N 2840/60* (2013.01); *C12N 2840/85* (2013.01)

(58) Field of Classification Search
None
See application file for complete search history.

(56) References Cited

U.S. PATENT DOCUMENTS

| | | | |
|---|---|---|---|
| 6,027,915 | A | 2/2000 | Morris et al. |
| 6,309,841 | B1 | 10/2001 | Morris et al. |
| 6,312,951 | B1 | 11/2001 | Morris et al. |
| 2011/0212518 | A1 | 9/2011 | Singh et al. |
| 2011/0281286 | A1 | 11/2011 | Yamazaki et al. |
| 2013/0236957 | A1 | 9/2013 | Singh et al. |
| 2014/0038233 | A1 | 2/2014 | Yoon et al. |

FOREIGN PATENT DOCUMENTS

| | | |
|---|---|---|
| EP | 2719764 A2 | 4/2014 |
| JP | 2011-152124 A | 8/2011 |
| KR | 10-2008-004 7319 A | 5/2008 |
| KR | 10-2012-0112254 A | 10/2012 |
| KR | 10-2014-0015999 A | 2/2014 |
| WO | 2010-023787 A | 3/2010 |
| WO | 2012/046255 A2 | 4/2012 |
| WO | 2014/017851 A2 | 1/2014 |

OTHER PUBLICATIONS

International Search Report from PCT/KR2015/006098 (dated Sep. 3, 2015).
Written Opinion from PCT/KR2015/006098 (dated Sep. 3, 2015).
Kim et al., "CHO cells in biotechnology for production of recombinant proteins: current state and further potential," *Appl Microbiol Biotechnol.*, 93:917-930 (2012).
GenBank Accession No. AC126686, Mus musculus BAC clone RP23148C24 from 18, complete sequence (Nov. 8, 2003).
Palazzoli et al., "Landscape of chromatin control element patents: positioning effects in pharmaceutical bioproduction," *Nature Biotechnology*, 29(7):593-597 (Jul. 2011).
Extended European Search Report from related European Patent Application No. 15810394.5 (dated May 9, 2017).
Kang et al., "A novel regulatory element (E77) isolated from CHO-K1 genomic DNA enhances stable gene expression in Chinese hamster ovary cells," Biotechnology Journal, 11(5):633-641 (May 2016).
Office Action from Japanese Patent Application No. 2016-574044 (dated Dec. 19, 2017).

*Primary Examiner* — Jim Ketter
(74) *Attorney, Agent, or Firm* — Merchant & Gould P.C.

(57) ABSTRACT

The present invention relates to a new gene fragment derived from Chinese hamster ovary (CHO) cell for enhancement of recombinant protein expression in animal cells and a use thereof. It has been found that using the vector comprising a gene fragment of the present invention enhances the expression of a target protein in animal cells. Accordingly, the vector comprising a gene fragment of the present invention could be usefully used in the production of biopharmaceuticals such as therapeutic antibodies, etc.

5 Claims, 9 Drawing Sheets

|  | CMV | E77-CMV | Ex77-CMV |
|---|---|---|---|
| Titer (μg/L) | 386.25 ± 22.98 | 1163.75 ± 12.37 | 636.25 ± 1.77 |
| Initial cell density (x $10^5$ cells/ml) | 5.67 ± 0.11 | 5.80 ± 0.38 | 3.68 ± 0.95 |
| Final cell density (x $10^5$ cells/ml) | 14.80 ± 1.13 | 11.85 ± 0.92 | 12.60 ± 1.41 |
| Specific productivity (pcd) | 0.12 ± 0.01 | 0.51 ± 0.04 | 0.31 ± 0.05 |

SEQUENCE LISTING

<160> NUMBER OF SEQ ID NOS: 15

<210> SEQ ID NO 1
<211> LENGTH: 2895
<212> TYPE: DNA
<213> ORGANISM: Artificial Sequence
<220> FEATURE:
<223> OTHER INFORMATION: Chinese hamster ovary K1 E77

<400> SEQUENCE: 1

```
ggatcattga gtgtacattc ttgtttgttt ttgatttggt ggtggtatag tgtgtggatt      60
taccctgctt ggtctttggt ttttgataaa gtggtattaa ctattaccta agttttagtg     120
agtgtagtta ccttccatat gttggagttt tccttccagt acattttag ggctggatta      180
gttgctaagt attgtttaaa tctggttttg tcatgaaata tcttgtttcc tccatctata     240
gtaattgaaa gctttgctgg gtatagttgt ctggactggc atctgtggac ttgaatgttt     300
gtagaatatc gatccacggc attctggctt tcagagtttc atggagaagt cacgtgtaat     360
tctgataggc ttgcctttat atgtgacttg gacttttccc tttgctgttc ctagtatttt     420
tactatactc tgtatatttg gtgtattagt tattatgtga agaggggact tctctgtggt     480
ctgctctatt tccgtgttct gtaagcttct tgtactttcc ttagcatgtc tttctttaga     540
ttgggaaagt tttcttctat ggttttgttg aatttgtact ctgtaccatt gacttggatt     600
tctttacttt cttctatact tattattctt aagttgggc ttttcatggt gtcccatatt      660
tcctggatat tttgtgttgt gatttgttgg acttaagatt ttctttgtct gtctgaaagc     720
cagaacctat ttctcctagt gtatcttcaa cgcttaaatt tctctcttcc atcttttgta     780
ttctgttctt tatgcatgcg tctctagttc ctcatcgttt aatcatcttt tcgaattcta     840
gcattccctc agactgcgtt tctattttt ccccgtctct atcttagctt tcaaacattg      900
ccctgtttga attgtttcct gcaaattttg gtttgccttt tcttccattt ctttgaagga     960
ttttctcatt tcctctgtta gggtctctgt gaaattcgtg aagttgtttt tacggtcttt    1020
ctgttctgct tcatctgcgc tgggatgttc aggtcttgct ggcatacagt ccctagactc    1080
tggtggtgtc atattggttt ttctgttttc aatgtgttct tatattttca tcatcccatc    1140
tcttgttcca gttggtgcag gtggtgtttc ttcctctcct tgtatgtaca ggcccaagtt    1200
tcttttgcag tgggtgcaaa agggtccaat actctgatgg tcctcacggt gtgtacagga    1260
gggtatgatg cactcccttt aaaggtgggt aggagcagaa ctagcacagc agaatcaagg    1320
ttgtttgttc ttcaggggt gagtccattt acttcgcagt ccccagtaca ggagttccca     1380
gagttggcag gttgaagttg ggcccaaaga caggggctga aactcagctc tgccctgaat    1440
gggaatggct aatagcccag cagactccca gttgcttggt ccacaaaaac tgtctcttct    1500
atcacagaga aaacagctgt tctatgaaag ttgatctcta cttggaaggt ataggcagaa    1560
aaatcagaaa ttaaaggtca tcattgactc catgattaat ttaaagcaag acaaaactaa    1620
atgaaattat gtccttaaaa attaataaca aattttagtt aaattcagcc acattgataa    1680
ccttaatcat tatcagaaat ttgcatggtt ttgttacatt ataaattggt ttccattatc    1740
tgtaacaact ttttctgtat atggtaaatt attttcctga atactaaact catctgtatc    1800
taaaataaca ttactgaatg tgagtttgca aagtagacct ctatgtgctt ttatttggct    1860
ttattatgaa accataccaa aggatacttg aaagagtttg ccatatttaa aggccatgtg    1920
agaaaagcag cagaaggcct ctctagattg gtagggatac actttcagag tagccacaag    1980
agcaatcaaa ttctgtattc tttgtcctcc actctgaaag cctttgttgg aagcatttct    2040
tgcccatggt aacagttacc atggagataa acatatcatc acagatggaa acagtgtccc    2100
taccaaacac tattcatcta gcctaaactt tcatagaagc tctccctgtg caaggagaaa    2160
ttgcacaatg atcctaatat agtttaggga attttaaaca gaatgtttct aggtgaattt    2220
```

| | |
|---|---|
| ggttcctaag atgttgactc acaaattcta cttattttat cctaatcatt aatcataatt | 2280 |
| ctagacaaga gctagtaaat ctcagttttc tagtatcatt tcccagtagt gagattatct | 2340 |
| atctatctat ctatctatct atctatctat ctatctatct atggagagat gcttcttttc | 2400 |
| atgattaatc acaaaagaaa ttttgtata aaatatagaa tttaggataa ttatatcaaa | 2460 |
| atgtgaaact aagcaaaaaa taaaatgaag actatcagtg tgtgtttcat gagcaagccc | 2520 |
| ttttcaggt cagctgtttc tgtgtatttc tccagcctag tacaggcaca ttgttaacca | 2580 |
| agaccaaact ttatattttc tcatgttttg tatgccaaat attttgtcat tgggagtatc | 2640 |
| agcaaatcag aggtgttatg aaagtgctag catatgttgt ggaattgcaa taataatgaa | 2700 |
| cttttaatt tgagcactat tatgtgtatt ctttatctga aacacttctt aaagtaccta | 2760 |
| aacttcagct gtgtctcagg actcaagaga taaacagatg catcttggtt agttcattgc | 2820 |
| cagattgagc tacatgaaaa tgatccagtt ttaaagaaac agctcacaca aaggtggtct | 2880 |
| tagcccttgg gatcc | 2895 |

<210> SEQ ID NO 2
<211> LENGTH: 1537
<212> TYPE: DNA
<213> ORGANISM: Artificial Sequence
<220> FEATURE:
<223> OTHER INFORMATION: Chinese hamster ovary K1 E77-t1

<400> SEQUENCE: 2

| | |
|---|---|
| ggatcattga gtgtacattc ttgtttgttt ttgatttggt ggtggtatag tgtgtggatt | 60 |
| taccctgctt ggtctttggt ttttgataaa gtggtattaa ctattaccta agttttagtg | 120 |
| agtgtagtta ccttccatat gttggagttt tccttccagt acatttttag ggctggatta | 180 |
| gttgctaagt attgtttaaa tctggttttg tcatgaaata tcttgtttcc tccatctata | 240 |
| gtaattgaaa gctttgctgg gtatagttgt ctggactggc atctgtggac ttgaatgttt | 300 |
| gtagaatatc gatccacggc attctggctt tcagagtttc atggagaagt cacgtgtaat | 360 |
| tctgataggc ttgccttat atgtgacttg gacttttccc tttgctgttc ctagtatttt | 420 |
| tactatactc tgtatatttg gtgtattagt tattatgtga agaggggact tctctgtggt | 480 |
| ctgctctatt tccgtgttct gtaagcttct tgtacttttcc ttagcatgtc tttctttaga | 540 |
| ttgggaaagt tttcttctat ggttttgttg aatttgtact ctgtaccatt gacttggatt | 600 |
| tctttacttt cttctatact tattattctt aagttggggc ttttcatggt gtcccatatt | 660 |
| tcctggatat tttgtgttgt gatttgttgg acttaagatt ttctttgtct gtctgaaagc | 720 |
| cagaacctat ttctcctagt gtatcttcaa cgcttaaatt tctctcttcc atcttttgta | 780 |
| ttctgttctt tatgcatgcg tctctagttc ctcatcgttt aatcatcttt tcgaattcta | 840 |
| gcattccctc agactgcgtt tctattttt ccccgtctct atcttagctt tcaaacattg | 900 |
| ccctgtttga attgtttcct gcaaattttg gtttgccttt tcttccattt ctttgaagga | 960 |
| ttttctcatt tcctctgtta gggtctctgt gaaattcgtg aagttgtttt tacggtcttt | 1020 |
| ctgttctgct tcatctgcgc tgggatgttc aggtcttgct ggcatacagt ccctagactc | 1080 |
| tggtggtgtc atattggttt ttctgttttc aatgtgttct tatattttca tcatcccatc | 1140 |
| tcttgttcca gttggtgcag gtggtgtttc ttcctctcct tgtatgtaca ggcccaagtt | 1200 |
| tcttttgcag tgggtgcaaa agggtccaat actctgatgg tcctcacggt gtgtacagga | 1260 |
| gggtatgatg cactcccttt aaaggtgggt aggagcagaa ctagcacagc agaatcaagg | 1320 |
| ttgtttgttc ttcaggggt gagtccattt acttcgcagt ccccagtaca ggagttccca | 1380 |

-continued

```
gagttggcag gttgaagttg ggcccaaaga cagggctga aactcagctc tgccctgaat    1440
gggaatggct aatagcccag cagactccca gttgcttggt ccacaaaaac tgtctcttct    1500
atcacagaga aaacagctgt tctatgaaag ttgatct                            1537
```

<210> SEQ ID NO 3
<211> LENGTH: 1363
<212> TYPE: DNA
<213> ORGANISM: Artificial Sequence
<220> FEATURE:
<223> OTHER INFORMATION: Chinese hamster ovary K1 E77-t2

<400> SEQUENCE: 3

```
gatctctact tggaaggtat aggcagaaaa atcagaaatt aaaggtcatc attgactcca      60
tgattaattt aaagcaagac aaaactaaat gaaattatgt ccttaaaaat taataacaaa     120
ttttagttaa attcagccac attgataacc ttaatcatta tcagaaattt gcatggtttt     180
gttacattat aaattggttt ccattatctg taacaacttt ttctgtatat ggtaaattat     240
tttcctgaat actaaactca tctgtatcta aaataacatt actgaatgtg agtttgcaaa     300
gtagacctct atgtgctttt atttggcttt attatgaaac cataccaaag gatacttgaa     360
agagtttgcc atatttaaag gccatgtgag aaaagcagca gaaggcctct ctagattggt     420
agggatacac tttcagagta gccacaagag caatcaaatt ctgtattctt tgtcctccac     480
tctgaaagcc tttgttggaa gcatttcttg cccatggtaa cagttaccat ggagataaac     540
atatcatcac agatggaaac agtgtcccta ccaaacacta ttcatctagc ctaaactttc     600
atagaagctc tccctgtgca aggagaaatt gcacaatgat cctaatatag tttagggaat     660
tttaaacaga atgtttctag gtgaatttgg ttcctaagat gttgactcac aaattctact     720
tattttatcc taatcattaa tcataattct agacaagagc tagtaaatct cagttttcta     780
gtatcatttc ccagtagtga gattatctat ctatctatct atctatctat ctatctatct     840
atctatctat ggagagatgc ttcttttcat gattaatcac aaaagaaatt tttgtataaa     900
atatagaatt taggataatt atatcaaaat gtgaaactaa gcaaaaaata aaatgaagac     960
tatcagtgtg tgtttcatga gcaagcccct tttcaggtca gctgtttctg tgtatttctc    1020
cagcctagta caggcacatt gttaaccaag accaaacttt atattttctc atgttttgta    1080
tgccaaatat tttgtcattg ggagtatcag caaatcagag gtgttatgaa agtgctagca    1140
tatgttgtgg aattgcaata ataatgaact ttttaatttg agcactatta tgtgtattct    1200
ttatctgaaa cacttcttaa agtacctaaa cttcagctgt gtctcaggac tcaagagata    1260
aacagatgca tcttggttag ttcattgcca gattgagcta catgaaaatg atccagtttt    1320
aaagaaacag ctcacacaaa ggtggtctta gcccttggga tcc                     1363
```

<210> SEQ ID NO 4
<211> LENGTH: 5148
<212> TYPE: DNA
<213> ORGANISM: Artificial Sequence
<220> FEATURE:
<223> OTHER INFORMATION: Chinese hamster ovary K1 Ex77

<400> SEQUENCE: 4

```
ggagtcttta cacccataga tcattgacac acagtttgaa gaatgcctct ttctgcccgt      60
gcctccaccg ccaaagtcct gcccagcagg cagttgattc actggacacc attgccagaa     120
gctacggctt ccggagctgg ctactgctct gccggtttcc aaaactcttt cttttaacaa     180
```

-continued

| | |
|---|---|
| catctgccca tttaccctag tatagtagcc gctctgaggt tttcagatta ctttgcaaca | 240 |
| aaacgaccat tcctctgaaa tgtgttacag tacaccattc cccctgctgg ccaaacatag | 300 |
| ttactgcaac tgaaagccca acatcgcagc tccttagtcc tgggaagag atgcaggtaa | 360 |
| gcctggtgca atggcagata atcttataat ggagaacgtt ggatatctgt tggaaacctc | 420 |
| tttgcttctt acgtgaatgt gatgctagat gaggattatt gcttcctctt tgtgtgtgtg | 480 |
| tttgtatgtg tgtacatata tgtatatatg tatatatata tatatatata tatatatatt | 540 |
| tgatattaag aatcagatca tggcaaatgg gatattccta aagggaagag ataaaagtca | 600 |
| agcagagaac aaggaagatg taccaactat tgataaccta gaaagatgaa tgcatgatat | 660 |
| ggtggacacc caggatagtg atttataaat tggaagactt agaatgctta ctaaaaaggt | 720 |
| tgaccatatt gaatctggca tgctacatag caacacaaat agatcagaat catggccaaa | 780 |
| taggaaacag cattagcttg atgtctgctg ctttaatgtc caaataagg aaaaatcaag | 840 |
| agaatattac catattaacc gagacactca ttccatgtct gatgactcta ttactaaata | 900 |
| ccaaaagctg tagtctacaa ttggatatct agaaggcaat ttgcatgcca ctcagttatt | 960 |
| atctaaggat gaaatattaa aagcttagat gcatatttga atgaaaaaac aaaaaaaaat | 1020 |
| taccaattct atggactcct tggaaactta tatgattcag gaagtccaaa tgctcaggga | 1080 |
| gacaatggtg agcagattac aggcctgaga ctaccttcaa tctgaaacct atgaatctga | 1140 |
| tacttttcaa agagggttaa aatcacctac accaatgttt cttttaagaa catgggtgcc | 1200 |
| ttgtatttgg ggcatagaaa ttcagaattg acacttcttc ctgacgggtt tttttttctg | 1260 |
| taatgaatat gaaatgtcct tcttcatgcc ttgattgatt ttagtttgaa gtctaatttg | 1320 |
| ttagatacta gcatacctac accagctggt ttcttgggtc cgtttgattg gaaaatctta | 1380 |
| tcccaatctt ttactctgag gaaatgtctg tctttgaagt tgaggttgtt tcttgtatgc | 1440 |
| agaggaagga tggattctgt cttttttatcc actctgttag cctgtgtctt tttataggtg | 1500 |
| agttaagacc attaatattg agggaaccca aggatcattg agtattcatt cttgtttgtt | 1560 |
| tttgatttgg cagtggtata gtgtgtggat ttaccctgct tggtctttgg ttttttgataa | 1620 |
| agtggtatta actattacct aagttttagt gagtgtagtt accttccata tgttggagtt | 1680 |
| ttccttccag tacatttta gggctggatt agttgctaag tattgtttaa atctggtttt | 1740 |
| gtcatgaaat atcttgtttc ctccatctat agtaattgaa agctttgctg ggtatagttg | 1800 |
| tctggactgg catctgtgga cttgaatgtt ggtagaatat ctatccatgg cattctggct | 1860 |
| ttcagagttt catggagaag tcacgtgtaa ttctgatagg cttccctta tatgttactt | 1920 |
| ggacttttcc ctttgctgcc ccaagtattt ttcctatact ctgtatattt ggtgttttag | 1980 |
| ttagtatgtg aagaggggac ttctctgtgg tctgctctat ttccgtgttc tgtaagcttc | 2040 |
| ttgtactttc cttagcatgt ctttctttag attgggaaag ttttcatcta tgattttgtt | 2100 |
| gaatttgtac tctgtaccat tgagttggat ttctttactt tctactatac ttattattct | 2160 |
| taagttaggg catttcatgg tatccatatt tcctggatat tttgtgttag tgatttgttg | 2220 |
| gacttaagat tttctttgtc caatgaacct atttctccta gtgtatcttc aatgcttaag | 2280 |
| tttctctctt tcatctcttg tattctgttc tttatgcttg cgtctctagt tcctcatcat | 2340 |
| ttagccatct tttctaattc tagctttccc gcagactgtg tttcttttttt tccccccatc | 2400 |
| tctatcttag ctttcaaaca ttgccctgtt tgaattgttt cttgcaaatt ttggtttgcc | 2460 |
| ttttcttcca tttctttgaa ggattttctc atttcctctg ttagggtctc tatcaaattc | 2520 |
| atgaagttgt ttttaaggtc tttctgttct gcttcatctg cattgggatg ttcaggtctt | 2580 |

```
gctggcatac agtccctaga ctctgctggt gtcatattgg ttttctgtt ttcaatgtgt    2640 tcttatattt tcgtcttccc atctcttgtt ccagttggtg caggtggtgt ttcttcctct    2700
ccttgtatgt acaggcccaa ggttcttttg cagtgggtgc aacagggtcc aatactccga    2760
tggttctcac agtgtgtaca ggagtgtctg aggcactccc tttaaaggtg ggtgggagca    2820
gaagtagcac agcagaatca aggttgtttg ttcttcaggg ggtgagtcca tttacttcgc    2880
agtccccagt acaggaattc ccagagttgg caggttgaag ttgggcccaa agacagggtc    2940
tgaaactcag ctctgccctg aatgggattg gctaatagcc cagcagattc ccagttgctt    3000
ggtccacaaa aacagtctct tctatcacag agaaaacagc tgttctatga aagttgatct    3060
gatttttaag gtttatttgg tttgttttat tttgttgatt ttcaaatgaa atggatttaa    3120
tctctcctca ccttaattga ctgcagggct tcaggctcta tccaggacag aagcctgaga    3180
cagctggtgg gaagcagaga tagttggagg ctctagctcc gtgggtgagc acatgcaaag    3240
cacgaggcca tggtggctgc ctggctcctt cgtcagggtt ttagctgata agttacccta    3300
gtgctgtagt tttgtatggg acctggaatg tccacacagt aactgtttaa aaagtattta    3360
gtttaacatt tgggagcatg tggtactcat tggacacatt ttaggagtca tttttctttt    3420
tccaactatg ggacctagag attaactcaa gatatcaggc ccctggtaaa tgcctcttcc    3480
cactgagaaa tcttgccagt ccaaaagcga atgggttcag cagggtgtat ttatatatta    3540
attcatttgt tttgcaaaaa tgcttaaaga ggaggagttg taataggtag agggtttcct    3600
caggcataag aggtacagga gtgaggaaaa tggtgagaaa ttacatgatt atatttcaat    3660
tatgttttaa aagaatgaag aattattgga ttttatctat catttcaaaa gttcaaattc    3720
attttcctat gagtgaacaa tgctctctgc ctttgcctcc cttctgtct ctccctctcc    3780 ttcaagagta aaaaaagac tttaatcaaa aacaagcaaa tgtgcccttg gaacaatcac    3840
aaaacaacac ccaagagggg gatggccaga ataacaacct atgaagcttc ataatcttca    3900
ggggacacct ccaggctcct ggcaaaaaac ttcagattct tgcctccaga aatgctaaag    3960
tcagtccttg ccacaccaca cttcatgaca tagagaatgt aaatgattcc ccttccaagt    4020
tggcaacact ctactgtttc tgggttctcc aatctgattc cagcactcat taactttgca    4080
accttaagca aatcatagaa ctccttcctc tgtctcagtt tactgccctg aatgtggagg    4140
gctcttccag atgagctagc ctttactctg ttaatgccac agttgttgtt ctaaacagtc    4200
tttattttca ttgttaaatg agtatttgaa tgtttttatt ttttcattct ttttgatgac    4260
attgtgaata tggacatgat attcaggtct agagaatatt atacagggc caaaattcca    4320 agccttggtt agacaggaat aggcaattct agctgggata aaaatatagg tcagattagg    4380
aataataatg acccatagaa cttcccaatg gggtgctatg ttggtatggt atctcttagc    4440
aagggcctac tatgcctcgg cctctcaact tcccttcagg aataaggtct tgttcaattg    4500
aacttggtac tgatggaaga agactcatgt gtcgaagttt ggtaaattct gcaatctgtg    4560
agactttcaa catggcagtt gaaaacact ggactctact tgtgttctct ggtatgtctg    4620 cccccttgagg gctaatttc ctcaggagag gtcatagaat gcttgtccaa tgaagatagg    4680
gtttctttca atactttagg aaagctatac attacaggaa agttatcttg cttttttgaaa    4740 caggaagatg gagaaacttt cccttgagta actcctaact ccacatagca aaaggaaag    4800 aaatcttagc cattgctctt ctgtcatgaa atacttcact ttttgtttaa tcatttatct    4860
tttattttgg tcaactaaaa tatggaaaaa tatacacatg gtcacagcct agaatttcac    4920
```

-continued

```
ttaaaggaac agcaaacttt cagatccaat aggtcgaatt cagggagata gatgccccat    4980
acattcctca ctctgagata gctgacaaga attaccgggc tacttaaaat actactgctg    5040 tctaacccttt tcctgtcttt atgtttcact tgtgtgaaat atgtaatcca tgtgaatgtg    5100
catgtgatgt aattccctgt gctaatgcaa acagatctta gaagaacc                 5148
```

<210> SEQ ID NO 5
<211> LENGTH: 20
<212> TYPE: DNA
<213> ORGANISM: Artificial Sequence
<220> FEATURE:
<223> OTHER INFORMATION: Primer Sequence gDNA-F

<400> SEQUENCE: 5

```
gggccagata tacgcggatc                                                  20
```

<210> SEQ ID NO 6
<211> LENGTH: 20
<212> TYPE: DNA
<213> ORGANISM: Artificial Sequence
<220> FEATURE:
<223> OTHER INFORMATION: Primer Sequence gDNA-R

<400> SEQUENCE: 6

```
ataatcaatg tcaacggatc                                                  20
```

<210> SEQ ID NO 7
<211> LENGTH: 20
<212> TYPE: DNA
<213> ORGANISM: Artificial Sequence
<220> FEATURE:
<223> OTHER INFORMATION: Primer Sequence cae-CM-R

<400> SEQUENCE: 7

```
ccgtcattga cgtcaatagg                                                  20
```

<210> SEQ ID NO 8
<211> LENGTH: 20
<212> TYPE: DNA
<213> ORGANISM: Artificial Sequence
<220> FEATURE:
<223> OTHER INFORMATION: Primer Sequence cae-seq-F

<400> SEQUENCE: 8

```
caattgcatg aagaatctgc                                                  20
```

<210> SEQ ID NO 9
<211> LENGTH: 20
<212> TYPE: DNA
<213> ORGANISM: Artificial Sequence
<220> FEATURE:
<223> OTHER INFORMATION: Primer Sequence cae-seq-R

<400> SEQUENCE: 9

```
ctatgaacta atgaccccgt                                                  20
```

<210> SEQ ID NO 10
<211> LENGTH: 38
<212> TYPE: DNA
<213> ORGANISM: Artificial Sequence
<220> FEATURE:
<223> OTHER INFORMATION: Primer Sequence E77-F

<400> SEQUENCE: 10

```
tacgggccag atatacgcgg atcattgagt gtacattc                              38
```

```
<210> SEQ ID NO 11
<211> LENGTH: 39
<212> TYPE: DNA
<213> ORGANISM: Artificial Sequence
<220> FEATURE:
<223> OTHER INFORMATION: Primer Sequence E77-t1-R

<400> SEQUENCE: 11
gtcaataatc aatgtcaacg atcaactttc atagaacag                              39

<210> SEQ ID NO 12
<211> LENGTH: 40
<212> TYPE: DNA
<213> ORGANISM: Artificial Sequence
<220> FEATURE:
<223> OTHER INFORMATION: Primer Sequence E77-t2-F

<400> SEQUENCE: 12
tacgggccag atatacgcga tctctacttg gaaggtatag                             40

<210> SEQ ID NO 13
<211> LENGTH: 39
<212> TYPE: DNA
<213> ORGANISM: Artificial Sequence
<220> FEATURE:
<223> OTHER INFORMATION: Primer Sequence E77-R

<400> SEQUENCE: 13
gtcaataatc aatgtcaacg gatcccaagg gctaagacc                              39

<210> SEQ ID NO 14
<211> LENGTH: 42
<212> TYPE: DNA
<213> ORGANISM: Artificial Sequence
<220> FEATURE:
<223> OTHER INFORMATION: Primer Sequence Ex77-F

<400> SEQUENCE: 14
gggccagata tacgcggatc ggagtcttta cacccataga tc                          42

<210> SEQ ID NO 15
<211> LENGTH: 42
<212> TYPE: DNA
<213> ORGANISM: Artificial Sequence
<220> FEATURE:
<223> OTHER INFORMATION: Primer Sequence Ex77-R

<400> SEQUENCE: 15
ataatcaatg tcaacggatc ggttcttcta agatctgttt gc                          42
```

VECTOR COMPRISING GENE FRAGMENT FOR ENHANCEMENT OF RECOMBINANT PROTEIN EXPRESSION AND USE THEREOF

This application is a U.S. National Stage Application under 35 U.S.C. § 371 of International Patent Application No. PCT/KR2015/006098 filed Jun. 16, 2015, which claims the benefit of priority to Korean Patent Application No. 10-2014-0073443 filed Jun. 17, 2014, the disclosures of all of which are hereby incorporated by reference in their entireties. The International Application was published in Korean on Dec. 23, 2015 as WO 2015/194834.

TECHNICAL FIELD

The present invention relates to a new gene fragment derived from Chinese hamster ovary (CHO) cell for enhancement of recombinant protein expression in animal cells and a use thereof.

BACKGROUND ART

The production of animal cell lines with high productivity is related with an industrial utility value of the corresponding target protein to be produced, and a process therefor takes a long time and high costs. The first thing to consider when producing animal cell lines with high productivity is to produce a vector for efficiently expressing a recombinant protein to be produced. How to produce the structure of the vector may greatly influence the obtainment of production cell lines with a higher value in the future. The expression of a foreign gene inserted into animal cells becomes stable as it is inserted into chromatin. The expression rate may vary depending on the position inserted, and this may also affect the growth or metabolism of cells. The foreign gene inserted into the chromatin sometimes becomes extinct as time passes by. Thus, various researches have been conducted for minimizing the decrease in gene expression, and sorting the cell lines with an increased expression rate to the maximum. Additionally, the modification of the structure of the vector is known to have a great impact thereon.

One of the methods showing enhanced effects while maintaining the gene delivered from the outside in the cells is to use a cis-regulatory element. When introducing a gene which encodes a target protein into the cells by using the vector including the cis-regulatory element, the expression of a target protein may be maintained regardless of the insertion position of chromatin, and a role for enhancing expression may be performed. As representative examples, there are matrix attachment regions (MARs), universal opening elements (UCOEs), locus control regions (LCRs), insulator elements, stabilizing and anti-repressor elements (STARs), etc. The construction and application of a vector system using each gene element have been considered a very major field (Nature biotechnology, Vol. 29, 593-597, 2011).

Only an expression augmenting sequence element (EASE) is known as the cis-regulatory element originated from a gene of CHO cell, which is widely used as a therapeutic protein production cell line. Other than the EASE, the cis-regulatory element has been found in a gene originated from human or mouse through various methods. The EASE was discovered by finding out the genetic position of a vector inserted into the production cell line which expresses a great amount of Tumor Necrosis Factor Receptor (A E Morris et al., Animal cell technology, 1997). Most of the cis-regulatory elements discovered in the past are used industrially and commercially in companies which produce biopharmaceuticals. Thus, screening a new cis-regulatory element originated from the CHO cell gene by a method different form the past and possessing a recombinant vector including the same would be useful for a process of developing various biopharmaceuticals such as biosimilars, etc.

DETAILED DESCRIPTION OF THE INVENTION

Technical Purpose

A purpose of the present invention is to provide a recombinant vector for increasing an expression of a target gene, comprising a gene fragment consisting of any one of base sequence selected from the group consisting of SEQ ID NO: 1, SEQ ID NO: 2, SEQ ID NO: 3 and SEQ ID NO: 4.

Technical Means for Achieving the Technical Purpose

In order to achieve the above-mentioned purpose, the present invention provides a recombinant vector for increasing an expression of a target gene, comprising a gene fragment consisting of any one of base sequence selected from the group consisting of SEQ ID NO: 1, SEQ ID NO: 2, SEQ ID NO: 3 and SEQ ID NO: 4.

Advantageous Effects

According to the present invention, when Chinese hamster ovary (CHO)-K1 cell line is transformed with the vector comprising a new gene fragment derived from CHO cell for enhancement of recombinant protein expression, an expression ability of the target protein is increased. Accordingly, the vector comprising a gene fragment of the present invention could be usefully used in the production of biopharmaceuticals such as therapeutic antibodies.

BRIEF DESCRIPTION OF DRAWINGS

FIG. 3(a) is a graph showing a comparison of a difference between cell groups, and FIG. 3(b) is a graph showing a comparison of the degree of fluorescence between top 50 single cell lines in terms of GFP expression;

BEST MODE FOR CARRYING OUT THE INVENTION

Figure 1:
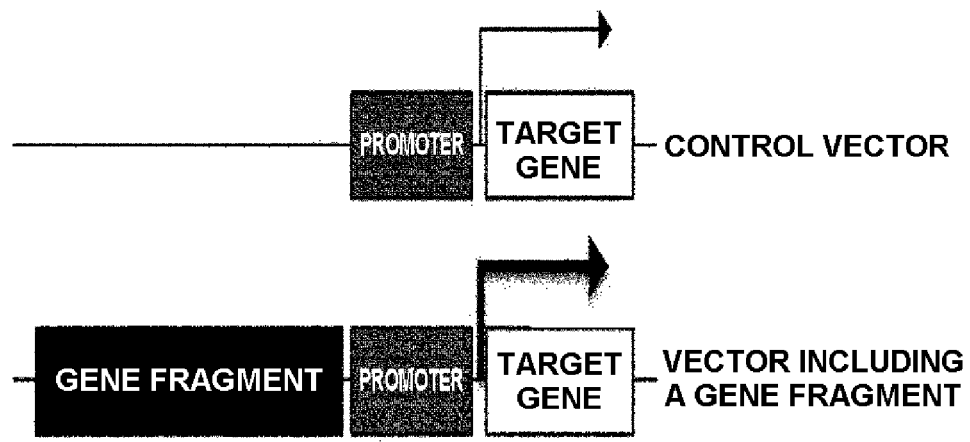
FIG. 1 is a schematic view of the present invention which enhances an expression of a target gene by inserting a gene fragment of an animal cell in front of a promoter.

Hereinafter, the present invention will be explained in detail.

The present invention provides a recombinant vector for increasing an expression of a target gene, comprising a gene fragment consisting of any one of base sequence selected from the group consisting of SEQ ID NO: 1, SEQ ID NO: 2, SEQ ID NO: 3 and SEQ ID NO: 4.

The term "vector" as used herein refers to a DNA construct including a foreign DNA sequence operably connected to a suitable regulatory sequence capable of expressing DNA in a suitable host. The vector according to the present invention may typically be constructed as a vector for an expression. Preferably, the vector according to the present invention is a vector for expressing a recombinant peptide or protein. Additionally, the vector according to the present invention may be constructed, having a prokaryotic cell or an eukaryotic cell as the host cell. The recombinant expression vector according to the present invention may, for example, be a bacteriophage vector, a cosmid vector, a yeast artificial chromosome (YAC) vector, etc. Considering the purpose of the present invention, it is preferable to use a plasmid vector. A typical plasmid vector which can be used for this purpose has a structure including (a) a replication origin allowing replication to be efficiently made so as to include hundreds of plasmid vectors per host cell, (b) antibiotic resistance gene so that the host cell transformed with the plasmid vector could be screened, and (c) a restriction site into which the foreign DNA fragment can be inserted. Even if a suitable restriction site does not exist, the vector and foreign DNA could be easily ligated by using a synthetic oligonucleotide adaptor or a linker. The vector used in the present invention may be constructed by various methods known in the related field. Additionally, a detailed method therefor is disclosed in Sambrook et al. Molecular Cloning. A Laboratory Manual. Cold Spring Harbor Laboratory Press (2001), and this publication is included as a reference in the specification of the present invention.

It is preferable that the gene fragment is inserted into the front of the target gene, the back of the target gene, or the front and back of the target gene at the same time, but is not limited thereto.

According to a specific embodiment of the present invention, the gene fragment consisting of any one of base sequence selected from the group consisting of SEQ ID NO: 1, SEQ ID NO: 2, SEQ ID NO: 3 and SEQ ID NO: 4 is inserted into the front of the target gene, the back of the target gene, or the front and back of the target gene at the same time.

It is preferable that the polynucleotide is originated from the Chinese Hamster Ovary (CHO)-K1 cell, but is not limited thereto.

It is preferable that a promoter of the recombinant vector is a promoter originated from a virus or a mammal. Specifically, it is more preferable that the promoter is a cytomegalovirus (CMV) promoter, but is not limited thereto.

It is preferable that the vector includes a target gene, an internal ribosome entry site (IRES) and a screened gene. It is more preferable that the screened gene is a zeocin resistance gene (ZeoR), but is not limited thereto.

The gene fragment consisting of any one of base sequence selected from the group consisting of SEQ ID NO: 1, SEQ ID NO: 2, SEQ ID NO: 3 and SEQ ID NO: 4 is screened by a method below, but is not limited thereto:

1) obtaining a gene fragment derived from CHO-K1 cell line to constitute a vector library;

2) transducing CHO-K1 cell line with the vector library, culturing the CHO-K1 cell line transduced with the vector library in a selective medium, and then classifying cells with a higher expression rate of a fluorescent protein than the control group into which a vector without inserting the gene fragment is introduced;

3) culturing the cells classified in the step 2) as a single clone and finding the gene fragment introduced; and 4) analyzing a sequence of the gene fragment found.

Additionally, the present invention provides a method for producing a target gene by using the recombinant vector, specifically a method for producing a target gene, comprising the steps of:

1) producing a recombinant vector for increasing an expression of target gene;

2) transforming an animal cell with the recombinant vector; and 3) culturing the animal cell transformed with the recombinant vector to obtain a protein produced.

Hereinafter, examples are provided to explain the present invention more specifically. According to the summary of the invention, it would be obvious to a skilled person in the art to which the present invention belongs that the scope of the present invention would not be limited by these examples.

Example 1: Production of Vector Library into which Cho Cell Gene Fragment is Inserted In order to achieve the purpose of the present invention, a method for constructing a green fluorescent protein expression vector and inserting a gene fragment of CHO-K1 cell line (ATCC® CCL-61™) thereinto to obtain the library was conducted. First, a genome of CHO-K1 cell line was obtained from CHO-K1 cell by using a DNeasy blood & tissue kit (Qiagen). The extracted genome DNA was made as a fragment followed by treatment under various conditions with different concentrations, temperatures and times for treating restriction enzyme Sau3AI (NEB). The Sau3AI restriction enzyme diluted twice up to 10 times from 2 unit per DNA 1 μg was reacted, the reaction was conducted per time at each temperature of 37° C., 25° C., 16° C. and 4° C., and DNA whose reaction was terminated was subjected to electrophoresis in agarose gel. DNA was extracted per size by using a gel extraction kit (Qiagen) from agarose gel where electrophoresis was performed, and DNA was used as a gene fragment to be inserted into the vector.

The green fluorescent protein expression vector, with an animal cell expression vector pcDNA3.1/Zeo (Invitrogen) as a basic vector, was constructed by inserting eGFP into NheI and XbaI restriction enzyme positions of a multicloning site. For the insertion of the gene fragment treated with Sau3AI, BamHI restriction enzyme sequence was generated at a position where the CMV promoter starts and was named GFP/pcDNAZeo. The BamHI restriction enzyme and CIAP were treated to the constructed vector to ligate the prepared gene fragment, and the vector comprising the gene fragment was introduced into *E. coli* DH5α. The *E. coli* into which the vector was introduced was plated into solid medium plates including ampicillin and was cultured for one night at 37° C. The number of colonies grown on the plates was checked, the plates were classified according to the size of the inserted gene fragment, and the colonies were collected in LB medium flask. The colony collected in one flask was cultured for about 3 hours and then the vector was obtained by using a DNA plasmid midi kit (Qiagen). Each sample obtained was called a DNA pool and was used as the vector library.

Example 2: Transduction and Cell Classification

The vector library produced in Example 1 was transduced into the CHO-K1 cell line, a cell group which expresses the green fluorescent protein in a various way through culturing in the selective medium was obtained, and cells with a higher fluorescence value than the control group were classified through a fluorescence-activated cell sorter (FACS).

Specifically, the CHO-K1 cell line was cultured in the RPMI1640 (Gibco) medium which includes 10% of FBS (fetal bovine serum, Gibco), and transduction was performed by using Lipofectamine 2000 (Invitrogen) according to the manufacturer's instructions. After 48 hours of transduction, the cells were separated by treating trypsin, moved to the selective medium including zeocin (Invitrogen) to be 10% v/v, and cultured for 2 weeks. A cell group into which the GFP/pcDNAZeo vector without inserting the gene fragment was introduced also was generated through the same process, and the cell group was used as the control group when classifying a high expression group of cells using the fluorescence-activated cell sorter (FACSAria, BD) (FIG. 1).

As a result, it was confirmed that a rate of cells with higher fluorescent protein expression than the control group is from about 0.1 to 0.2%, and the cells were separated to obtain cells.

Example 3: Formation of Single Cell Line and Gene Fragment Analysis

The cells classified in Example 2 were cultured as a single cell line and the gene fragment which the vector introduced into each cell has was identified.

Specifically, the classified cells were placed into 96 well plates with 1 cell/well in order to obtain single cell lines thereof, cultured for about 2-3 weeks, and measured the GFP of degree of fluorescence by the microplate reader (Bioteck). Through this, about 100 single cell lines with a high degree of fluorescence were screened, and the screened cells were cultured in T25 flask until it reaches confluent state. Afterwards, each cell was separated from the flask, a GFP mean value was obtained by using a flow cytometry, and the expression of each cell line was compared therethrough. In order to confirm which gene fragment inserted into the vector the cell lines with high expression level have, a genome DNA was extracted from each cell and used as a template, and PCR was performed by using primers in Table 1 below. The primer was produced by taking front and back sequences based on BamHI restriction enzyme in front of the CMV promoter of the vector. In order to confirm the inserted gene sequence, a total of 30 PCR reactions were carried out for amplification under conditions of 1 min at 95° C., 1 min at 60° C., and 4 mins at 72° C. by using a cae-seq-F primer (SEQ ID NO: 8) and a cae-sea-R primer (SEQ ID NO: 9). As to the genes of clones for which a proper PCR amplification was not performed properly, a cae-CM-R primer (SEQ ID NO: 7) corresponding to a middle portion of the CMV promoter was used as a reverse primer. In this case, the ones which brought the PCR product of about 300 bp were classified as the clone with the vector into which the gene fragment is not inserted and is generated by self-ligation.

TABLE 1

Primer sequences for confirming the insertion of CHO-K1 gene fragment and the cloning thereof

| SEQ ID NO. | SEQ Name | Primer direction | Sequence (5'→3') |
|---|---|---|---|
| 5 | gDNA-F | Forward direction | GGG CCA GAT ATA CGC GGA TC |
| 6 | gDNA-R | Reverse direction | ATA ATC AAT GTC AAC GGA TC |
| 7 | cae-CM-R | Reverse direction | CCG TCA TTG ACG TCA ATA GG |
| 8 | cae-seq-F | Forward direction | CAA TTG CAT GAA GAA TCT GC |
| 9 | cae-seq-R | Reverse direction | CTA TGA ACT AAT GAC CCC GT |

As a result, it was confirmed that most sequences with a high fluorescence value had a gene fragment with a size of about 3 kb. As a result of sequence analysis of these PCR products, it could be confirmed that they had similar sequences. The PCR was performed for the gene of cell line No. 77 with a highest fluorescence value by using gDNA-F primer (SEQ ID NO: 5) and gDNA-R primer (SEQ ID NO: 6). The PCR product was inserted into the BamHI site of the GFP/pcDNAZeo vector constructed in Example 1 by using an In-fusion HD cloning kit (clontech). Thereafter, an entire sequence was analyzed. The E77 sequence was called SEQ ID NO: 1, and a result of the entire sequence analysis was inputted in Blast of NCBI and CHOgenome websites and then analyzed. As a result of analysis, it was confirmed that E77 is DNA with a size of 2895 bp, and two fragments among the CHO-K1 gene are linked. It was confirmed that the front sequence had 95% homology with the sequence of AFTD01141246 4170-5698bp, and this sequence was called E77-t1 (SEQ ID NO: 2). It was confirmed that the back sequence has 99% homology with the sequence of AFTD01082471 13582-15021 bp, and this sequence was called E77-t2 (SEQ ID NO: 3).

Example 4: Analysis for Effect of E77 Using Green Fluorescent Protein

Figure 2A:
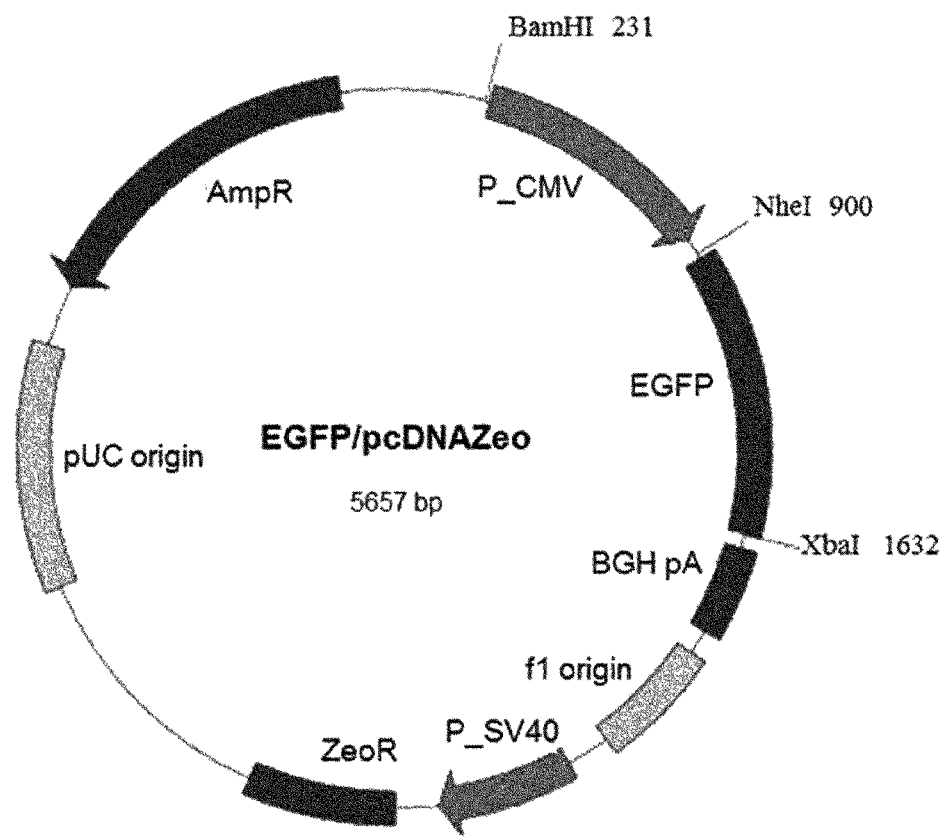
FIG. 2(a) is a view illustrating EGFP/pcDNAZeo vector and FIG. 2(b) is a view illustrating EGFP/pcDNAZeo-E77 vector.
Figure 2B:
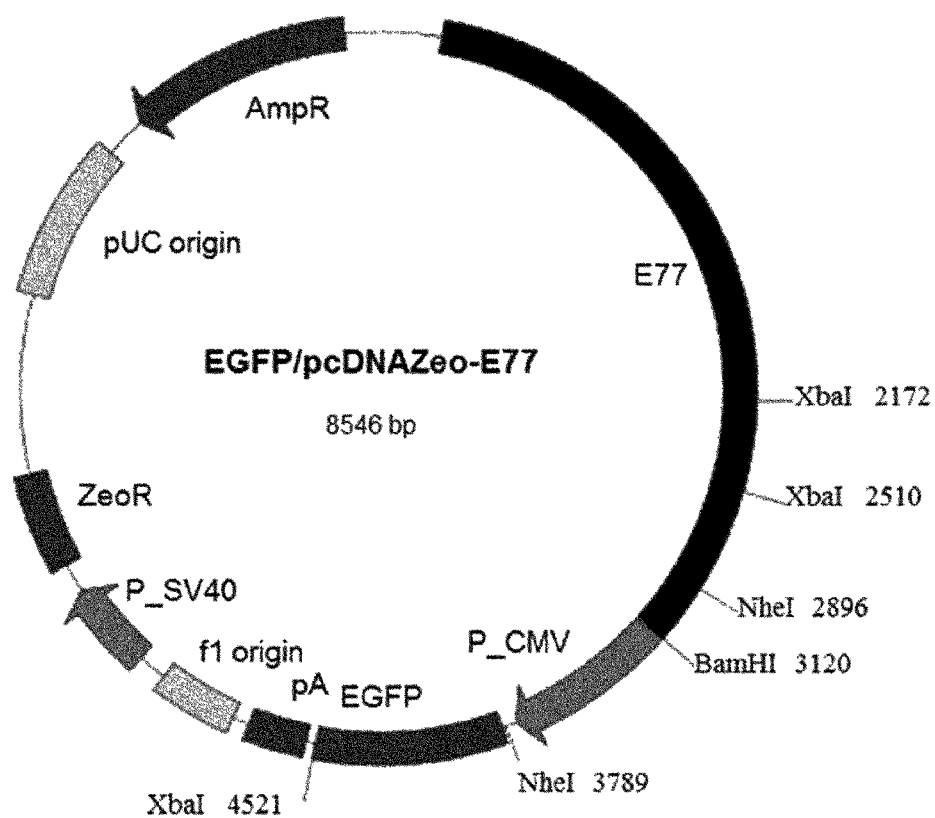

In order to verify the effect of E77 (SEQ ID NO: 1) obtained in Example 3, the transduction was performed on the CHO-K1 cell line by using the control vector GFP/pcDNAZeo (FIG. 2(a)) into which the gene fragment is not inserted, and the vector GFP/pcDNAZeo-E77 (FIG. 2(b)) into which E77 is inserted, and the expression of green fluorescent protein was checked.

Specifically, after 48 hours of transduction of each vector, the cells with concentration of $1\times10^4$ cells/ml in the zeocin selective media were put in each flask and cultured for about 2-3 weeks, thereby forming stable cell groups. Additionally, after 48 hours of transduction, the cells were put into 96 well plates with 50 cells/well by using a limited dilution method, about 100 single clones were obtained for each cell group, and the fluorescence value for each cell was measured.

Figure 3A:
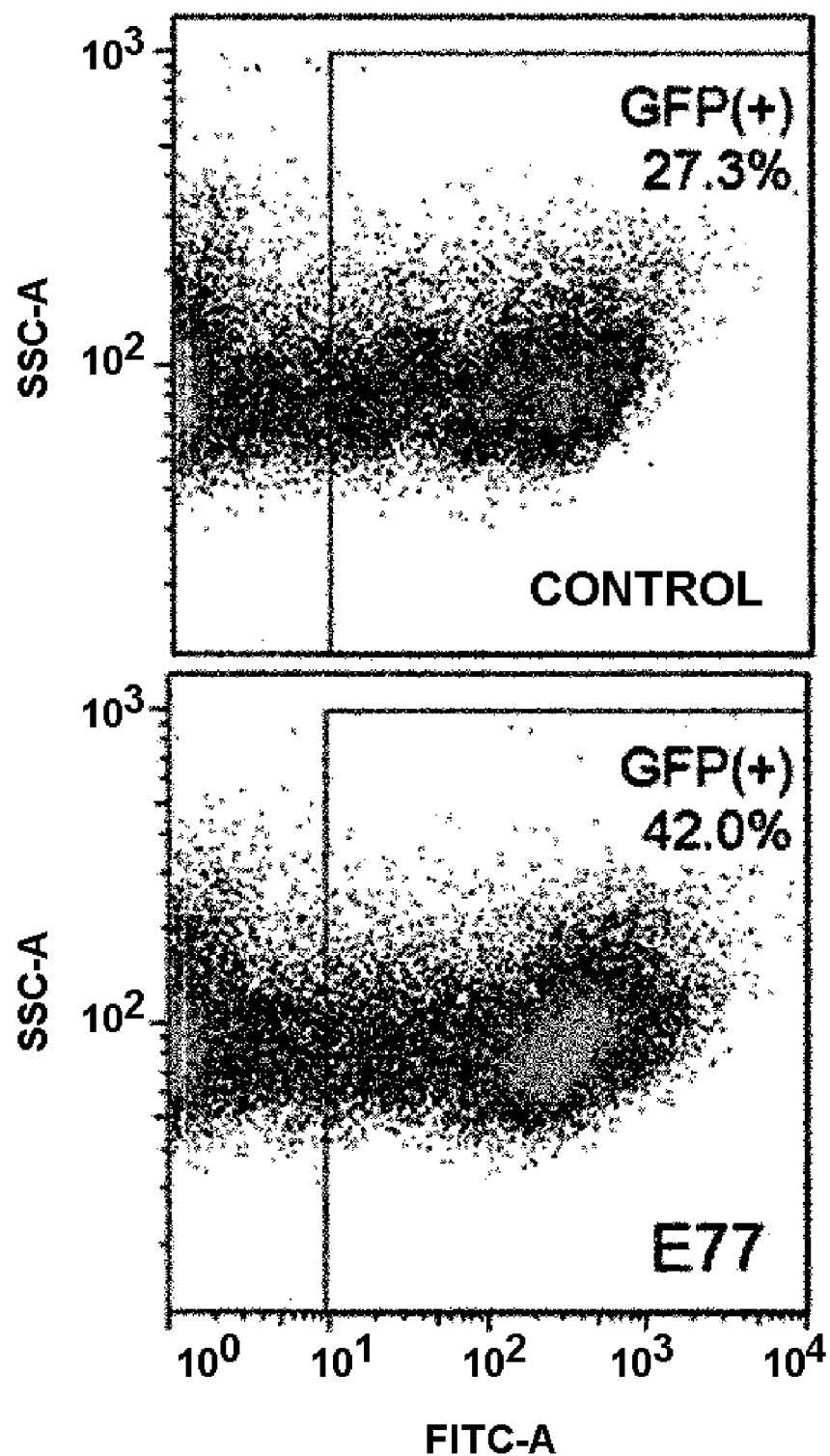
FIG. 3(a) and FIG. 3(b) are graphs verifying that E77 attributes to formation of a cell line with enhanced degree of fluorescence.
Figure 3B:
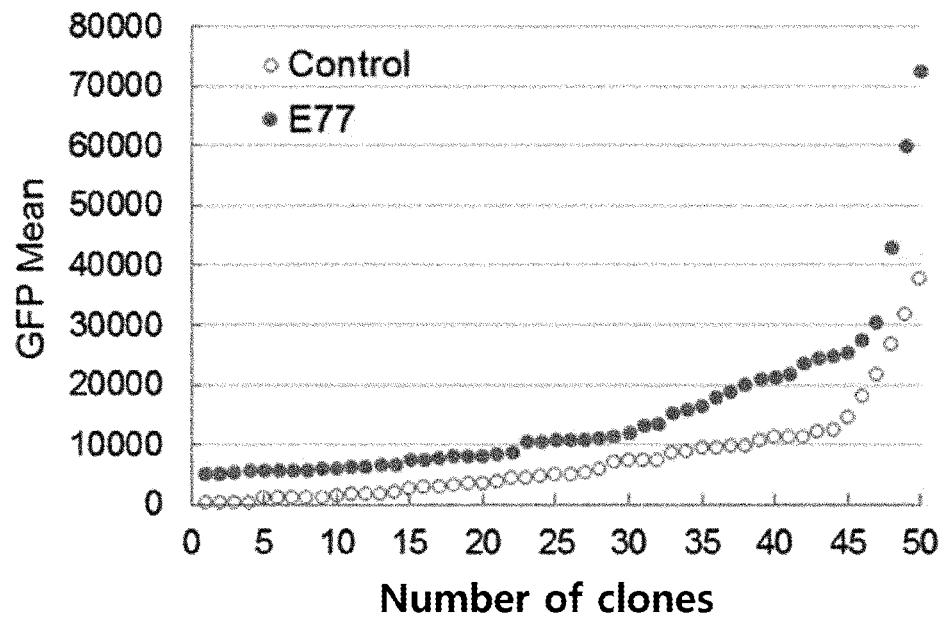

As a result, when forming the entire cell as a stable cell group, the rate of cell expressing GFP is 27.3% compared to the control group. In comparison, in the case of cell group into which the vector comprising E77 is introduced, the expression rate was 42% (FIG. 3(a)). The number of single cell lines obtained in the plates with the same number was 84 for the control group and 114 for E77. Among them, the number of cell lines which express GFP was 50 and 80, respectively, of which GFP expression rates are 59.5% and 70% with respect to the total number. Among these screened single cell lines, the number of cell lines of which fluorescence value is over 20000 was 4 for the control group and 13 for E77. It was confirmed from the comparison of 50 cell lines with high fluorescence value of GFP that there is a difference in expression level of entire GFP (FIG. 3(b)). Accordingly, it was confirmed that in the case of inserting E77 in front of the CMV promoter, the cells with enhanced expression level of GFP, which is the target protein, could be obtained much more than the control group.

Figure 4A:
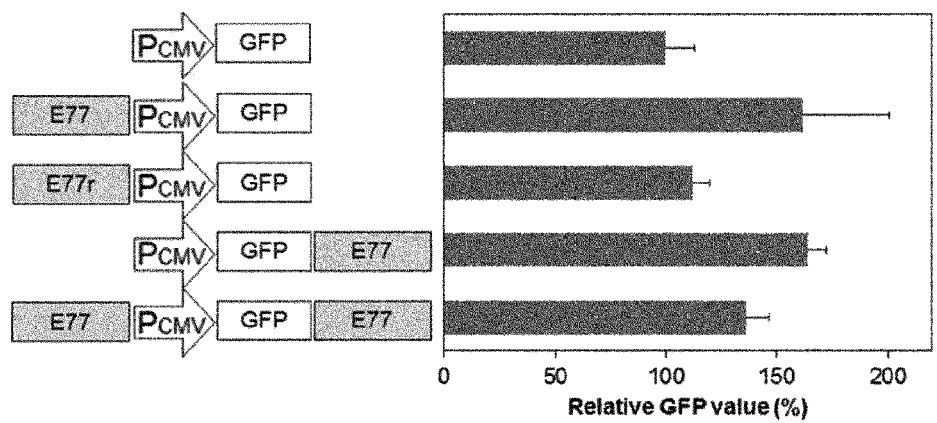
FIG. 4(a) is a diagram illustrating a part of a vector including E77 (SEQ ID NO:1) and E77 reverse order at the 5' portion of a CMV promoter of a pGIZ vector respectively, a vector including E77 at the 3' portion, and a vector including E77 at both 5' and 3' portions, and a graph showing a comparison of a difference in expression of the degree of fluorescence according to these vectors.

Example 5: Analysis for E77 Effect According to Direction and Position in Vector It is known that the effects of some elements in the cis-regulatory element could be improved according to the direction in which the vector is inserted or the positional relation with the target gene. Accordingly, in the case of E77, it was checked whether E77 had directional properties of being inserted into the vector and effects according to the position. When forming cell groups and comparing the degree of fluorescence shown by the cell groups, there were many cells which did not express GFP when the selective marker was expressed by a promoter separated from the CMV promoter. Thus, in order to reduce an error resulting therefrom, the vector was constructed to be expressed in the form of GFP-IRES-ZeoR by using the IRES so as to be expressed green fluorescent protein which intends to express and zeocin resistance gene (ZeoR), which is the selective marker, as one transcription unit. The IRES was obtained from pIRES vector (clontech). After the PCR was performed on each gene of GFP, IRES and ZeoR, the IRES and ZeoR PCR products were used as templates for performing the second PCR. Then, the IRES-ZeoR PCR product and the GFP PCR product were used as templates for performing the third PCR, thereby obtaining GFP-IRES-ZeoR gene. The pcDNA3.1/Zeo vector was treated with PvuII restriction enzyme and was self-spliced to constitute the vector where zeocin resistance gene was removed. The GFP-IRES-ZeoR gene was inserted into its multi-cloning site to constitute the vector. This vector was called pGIZ. E77 (SEQ ID NO: 1) was inserted into the 5' portion of the CMV promoter in the constructed vector, and 77E insertion vector which puts the same in a reverse order was also constructed. Additionally, the vector which puts E77 at the 3' portion of GFP-IRES-ZeoR gene and the vector which puts the same at both the positions of 5' and 3' were also constructed (FIG. 4(a)). The cells transduced with the constructed vector forms a stable cell group through the selective medium culture. The degree of fluorescence of each cell group was compared by using flow cytometry (Guava, Millipore). The vector which puts E77 at the 5' portion in a reverse order does not show any improved effect compared to the control group, so it was observed that E77 has directional properties. The vector into which E77 was inserted at the 3' portion shows 50% increase of expression rate which is almost similar to the vector into which puts the same at the 5' portion. Also, the vector which puts E77 at the front and back shows 30% increase of expression rate.

Example 6: Analysis for Effect of Modified E77

As mentioned in Example 3, E77 consists of two gene fragments. Accordingly, the analysis was conducted as to whether the same effect as E77 could be shown only when each of the two gene fragments exists, and whether the sequence extending the gene portion to which the front gene fragment belongs to the front and back also has the effect.

Specifically, the front portion of the gene fragment constituting E77 (SEQ ID NO: 1) was called E77-t1 (SEQ ID NO; 2), and the back portion thereof was called E77-t2 (SEQ ID NO: 3). The sequence extending the gene to which E77-t1 fragment belongs was called Ex77 (SEQ ID NO: 4). Ex77 corresponds to 2639-7786 bp of AFTD01141246 obtained through the homology search of CHO-K1[ATCC]_genbank_contig nucleotide database among CHO genome database at www.chogenome.org. AFTD01141246 gene is a gene fragment (contig) belonging to a part of NW_003615552 gene (homology analysis of CHO-K1 [ATCC]_refseq_scaffold database), and since the role of the gene has not been clarified yet, the gene fragment inserted into the corresponding vector was obtained as below. The vector including E77 was used as a template, the gene fragment obtained by performing PCR using the primers E77-F (SEQ ID NO: 10) and E77-t1-R (SEQ ID NO: 11) was called E77-t1 (SEQ ID NO: 2), and the gene fragment obtained by performing PCR using the primers E77-t2-F (SEQ ID NO: 12) and E77-R (SEQ ID NO: 13) was called E77-t2 (SEQ ID NO: 3). Ex77 (SEQ ID NO: 4) was obtained by performing the PCR using CHO-K1 genome DNA as a template, and using primers Ex77-F (SEQ ID NO: 14) and Ex77-R (SEQ ID NO: 15). The gene fragment obtained through the PCR was inserted into the BamHI position where the CMV promoter of pGIZ vector starts by using the In-fusion HD cloning kit. The primers used for PCR and In-fusion are as shown in Table 2 below.

The cells transduced with the pGIZ vector into which the gene fragment is inserted forms a stable cell group through the selective medium culture, and the degree of fluorescence of each cell group was compared by using flow cytometry (Guava, Millipore).

TABLE 2

Primer sequences for gene fragment insertion

| SEQ ID NO. | Sequence name | Primer direction | Sequence (5'→3') |
|---|---|---|---|
| 10 | E77-F | Forward direction | TAC GGG CCA GAT ATA CGC GGA TCA TTG AGT GTA CAT TC |
| 11 | E77-t1-R | Reverse direction | GTC AAT AAT CAA TGT CAA CGA TCA ACT TTC ATA GAA CAG |
| 12 | E77-t2-F | Forward direction | TAC GGG CCA GAT ATA CGC GAT CTC TAC TTG GAA GGT ATA G |
| 13 | E77-R | Reverse direction | GTC AAT AAT CAA TGT CAA CGG ATC CCA AGG GCT AAG ACC |
| 14 | Ex77-F | Forward direction | GGG CCA GAT ATA CGC GGA TCG GAG TCT TTA CAC CCA TAG ATC |
| 15 | Ex77-R | Reverse direction | ATA ATC AAT GTC AAC GGA TCG GTT CTT |

Figure 4B:
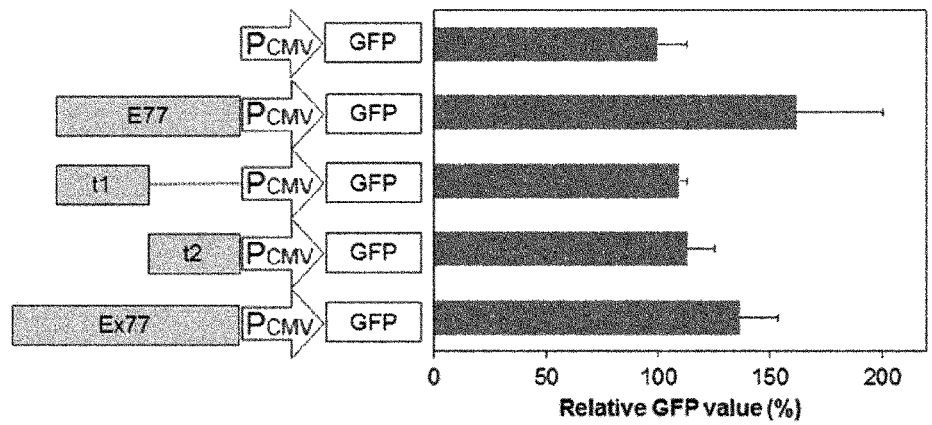
FIG. 4(b) is a diagram illustrating a part of a vector including E77 (SEQ ID NO: 1), E774-t1 (SEQ ID NO: 2), E77-t2 (SEQ ID NO: 3) and Ex77 (SEQ ID NO: 4) respectively, and a graph showing a comparison of a difference in expression of the degree of fluorescence according to these vectors. The histogram of FIGS. 4(c) to (f) is a graph showing a comparison of the degree of fluorescence expression between the cell groups formed according to each vector and the control group.
Figure 4C:
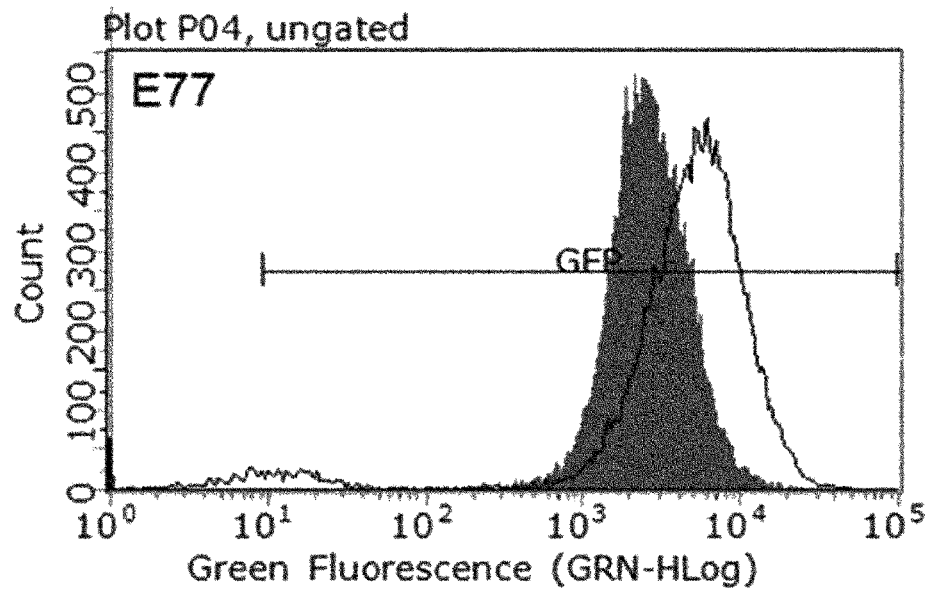
Figure 4D:
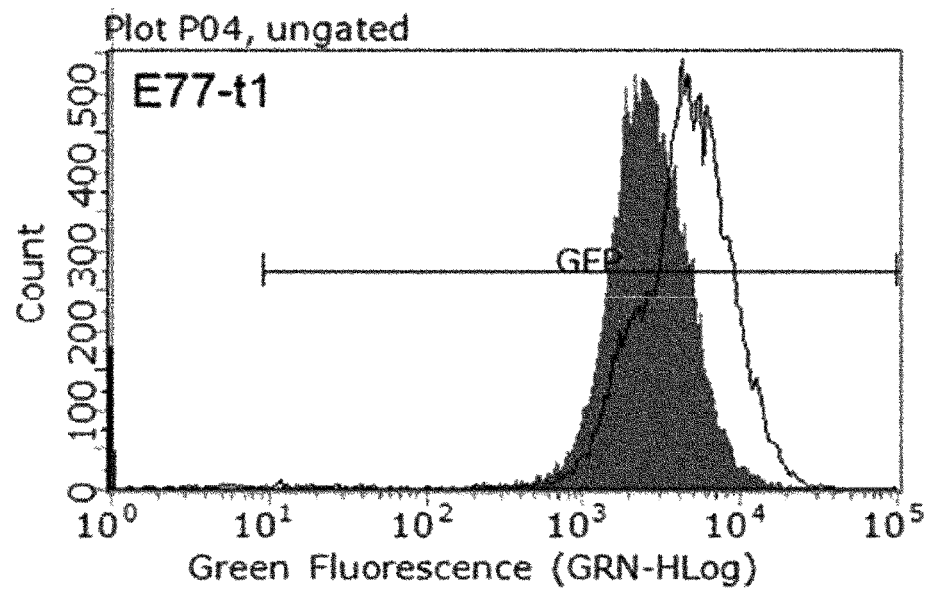
Figure 4E:
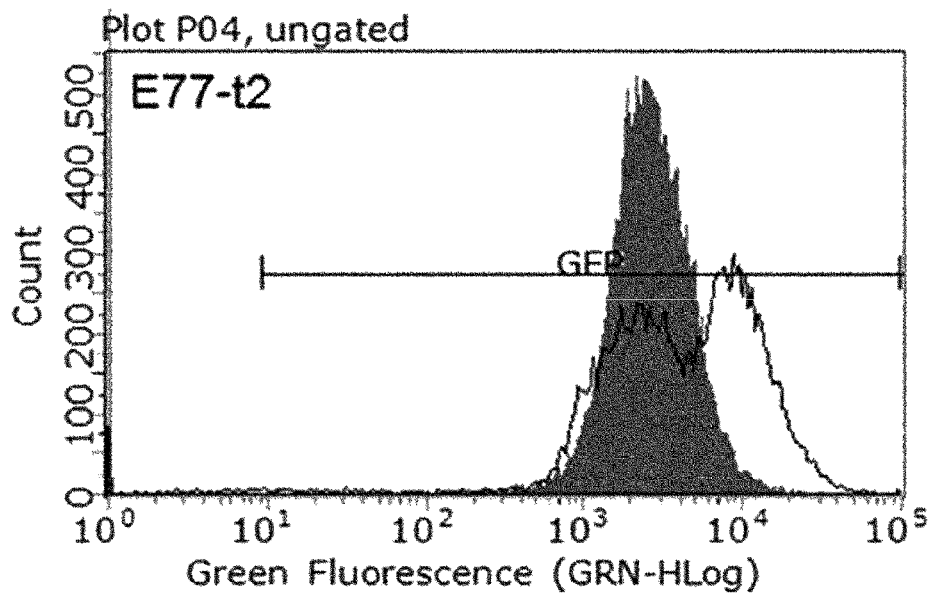
Figure 4F:
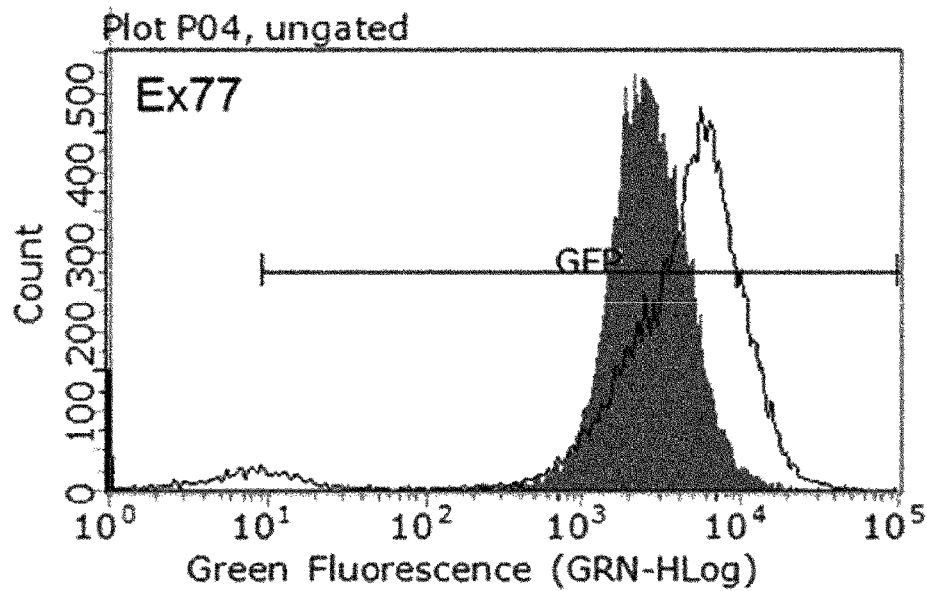

As a result of comparing fluorescence values between each cell group, it was confirmed that about 30 to 50% of cells had a higher expression level than the control group (FIG. 4(b)). Additionally, it was confirmed that the effect of gene fragments E77-t1 (SEQ ID NO: 2) and E77-t2 (SEQ ID NO: 3) is slightly lower than E77 (SEQ ID NO: 1), but is higher than the control group. Additionally, Ex77 (SEQ ID NO: 4) had a higher value than E77 (SEQ ID NO: 1). Through this result, it was confirmed that a part of sequence E77 (SEQ ID NO: 1) and the gene sequence to which the partial sequence belongs may also affect the enhancement of expression of the target protein (FIGS. 4(c), 4(d), 4(e) and 4(f)).

Example 7: Analysis for Yield of Antibody of Vector Using E77

In order to confirm whether E77 (SEQ ID NO: 1) and Ex77 (SEQ ID NO: 4) affect the expression rate of a protein other than the fluorescent protein, the antibody production vector into which E77 (SEQ ID NO: 1) and Ex77 (SEQ ID NO: 4) are inserted was constructed and introduced into animal cells to measure the yield of the antibody.

Specifically, the antibody production vector was constructed to express from the CMV promoter as starting to the genes encoding the antibody heavy chain and light chain connected through IRES (Internal Ribosome Entry Site) in one transcription unit. In the same manner as the above experiment, E77 and Ex77 were inserted into the BamHI position in front of the CMV promoter. Since zeocin resistance gene is expressed by another promoter, IRES-GFP was connected to zeocin gene for constructing the internal control group so that green fluorescent protein could be expressed together. After transducing CHO-K1 cell line (ATCC® CCL-61™) with the constructed vector and forming a stable cell group in the selective medium, the staining was performed with the antibody to which PE, a fluorescent material, is coupled, and the cells showing top 5% of expression rate were classified by using a cell sorter. In order to measure the yield of antibody of the classified cells, cells were cultured on the plates with the concentration of $1\times10^5$ cells/ml, the culture medium was removed after 4 days of culture, and the number of cells was measured. The culture medium was subjected to centrifugation, supernatant was stored at 20° C., and the amount of antibody was measured later through an enzyme-linked immunosorbent assay. The enzyme-linked immunosorbent assay was performed by using IgG ELISA kit (Bethyl lab) and performed according to the manufacturer's instructions. The antibody fluorescence staining for the cells was performed again together with quantitative analysis to conduct qualitative analysis through the flow cytometry.

Figure 5A:
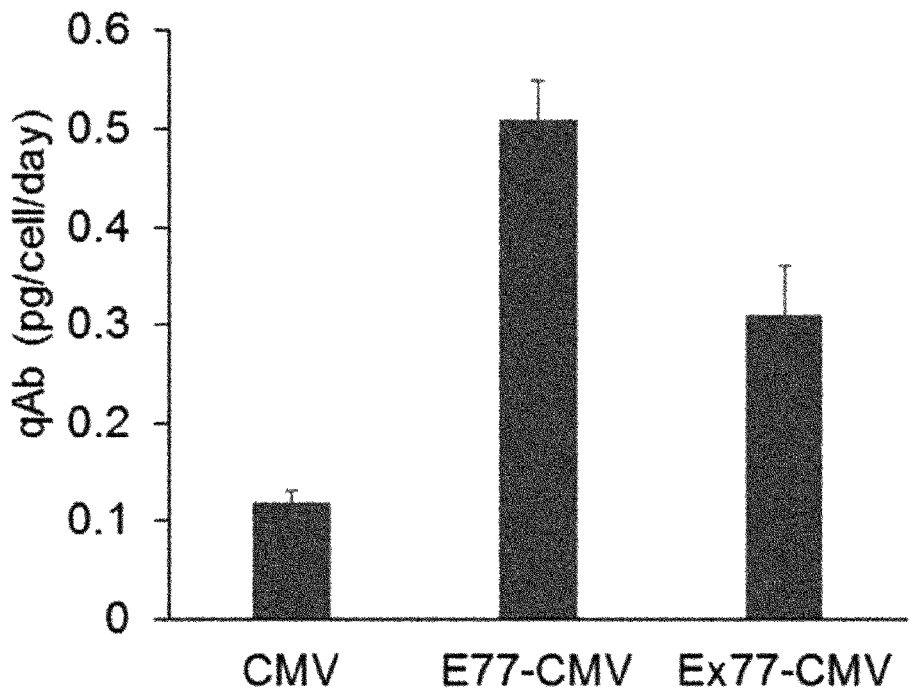
FIG. 5(a) is a graph showing the analysis result of the yield of an antibody per unit cell for the control group and the cell groups in which the antibody expression vectors including E77 and Ex77 respectively are introduced.
Figures 5B, 5C:
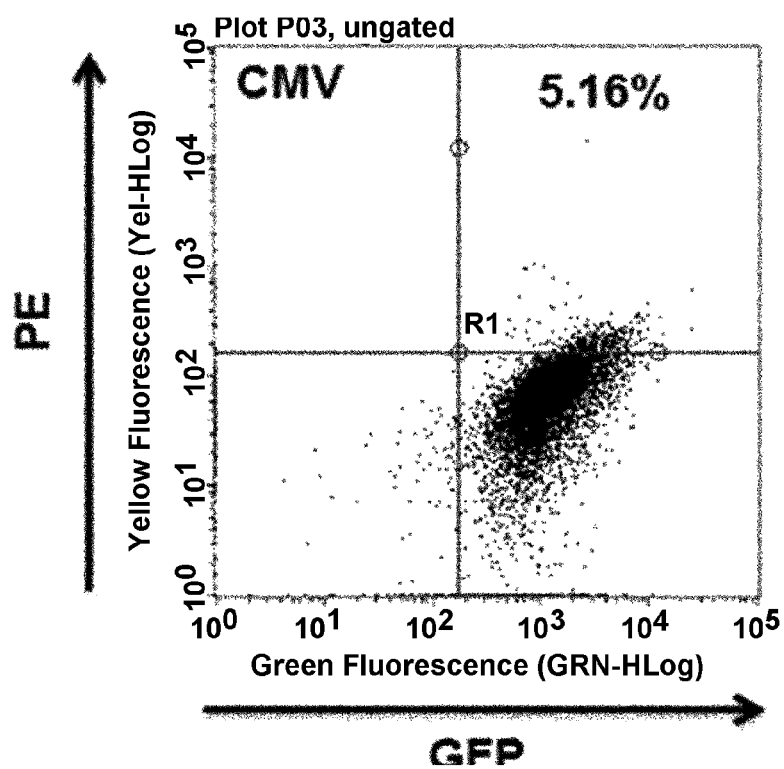
FIG. 5(b) is a detailed data for the graph (a). A dot plot of FIGS. 5(c) to 5(e) is the fluorescence analysis result of the yield of the antibody for each cell group.
Figure 5D:
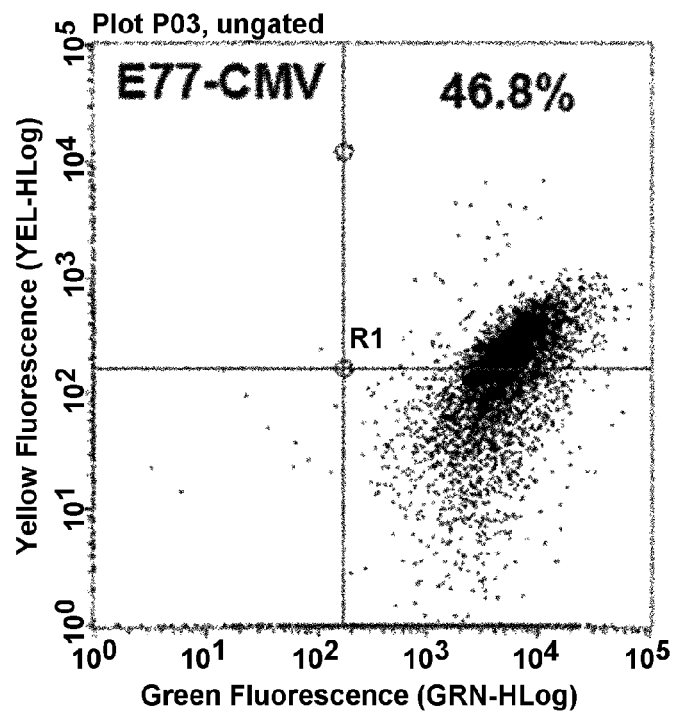
Figure 5E:
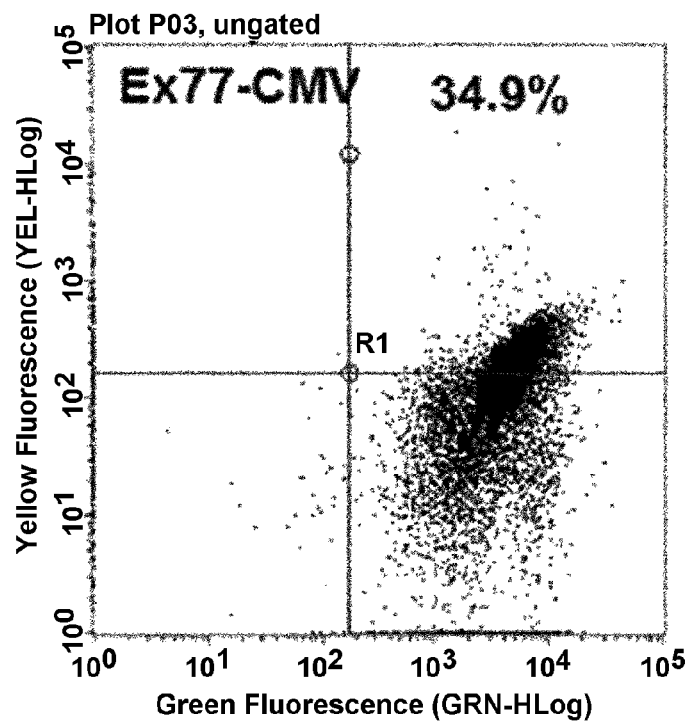

As a result of confirmation after the culture for 4 days, it was confirmed that the cell group into which the vector inserting E77 (SEQ ID NO: 1) was introduced showed the yield of antibody increased by three times and the yield increased about 5 times per unit cell compared to the control group. Additionally, the cell group into which the vector inserting Ex77 (SEQ ID NO: 4) was introduced showed the yield increased about 3 times per unit cell compared to the control group (FIGS. 5(a) and 5(b)). It was confirmed through the flow cytometry that in the control group, 5.16% of cells expresses the antibody. In comparison, in the case of cell group into which E77 (SEQ ID NO: 1) was introduced, 46.8% of cell expresses the antibody, and in the case of cell group introducing Ex77 (SEQ ID NO: 4), 34.9% of cells expresses the antibody. Thus, it was confirmed that the antibody expression rate is remarkably increased in the stably formed cell group (FIGS. 5(c), 5(d) and 5(e)).

What is claimed is:

1. A recombinant vector for increasing expression of a target gene, comprising a gene fragment consisting of a base sequence selected from the group consisting of SEQ ID NO: 1, SEQ ID NO: 2, SEQ ID NO: 3, and SEQ ID NO: 4.

2. The recombinant vector for increasing an expression of a target gene of claim 1, wherein the gene fragment is inserted upstream of the target gene, downstream of the target gene, or upstream and downstream of the target gene at the same time.

3. The recombinant vector for increasing an expression of a target gene of claim 1, further comprising a promoter originated from a virus or a mammal.

4. An animal cell transformed with the recombinant vector of claim 1.

5. A method for producing a target protein, comprising:
 1) producing a recombinant vector of claim 1;
 2) transforming an animal cell with the recombinant vector; and
 3) culturing the animal cell transformed with the recombinant vector to obtain the protein produced.

* * * * *